(12) United States Patent
Choi et al.

(10) Patent No.: US 7,223,590 B2
(45) Date of Patent: May 29, 2007

(54) PROCESS FOR PREPARING PRAVASTATIN SODIUM

(75) Inventors: Nam-Hee Choi, Seoul (KR); Kon-Tae Tak, Changwon-si (KR); Ki-Woo Lee, Seoul (KR); Nam-Hyun Kim, Busan (KR); Jong-Chang Jun, Andong-Si (KR); Yoon-Jeong Kong, Seoul (KR); Kyung-Mi Lee, Incheon (KR)

(73) Assignee: Kobiotech Co., Ltd. (KR)

( * ) Notice: Subject to any disclaimer, the term of this patent is extended or adjusted under 35 U.S.C. 154(b) by 381 days.

(21) Appl. No.: 10/490,937

(22) PCT Filed: Sep. 28, 2002

(86) PCT No.: PCT/KR02/01824

§ 371 (c)(1),
(2), (4) Date: Jun. 1, 2004

(87) PCT Pub. No.: WO03/042373

PCT Pub. Date: May 22, 2003

(65) Prior Publication Data

US 2004/0259216 A1    Dec. 23, 2004

(30) Foreign Application Priority Data

Sep. 29, 2001  (KR) .............................. 2001-60923

(51) Int. Cl.
*C12N 1/20*     (2006.01)
(52) U.S. Cl. ................................................ 435/252.35
(58) Field of Classification Search ........... 435/252.35, 435/41
See application file for complete search history.

(56) References Cited

U.S. PATENT DOCUMENTS

| 4,346,227 A | 8/1982 | Terahara et al. |
| 5,179,013 A * | 1/1993 | Matsuoka et al. .......... 435/125 |
| 5,830,695 A * | 11/1998 | Serizawa et al. .......... 435/69.1 |
| 2005/0153422 A1* | 7/2005 | Lin et al. ................. 435/252.3 |

FOREIGN PATENT DOCUMENTS

WO    WO - 98/45410 A1    10/1998

OTHER PUBLICATIONS

Castelli, *JAMA*, 256:2835, 1986.
Ito, S. et al., *Acta Cystallogr. D. Biol. Crystallogr.*, 55:1209-11, 1999.
Serizawa, N., *Bitechnol. Annu. Rev.*, 2:373-89, 1996.

* cited by examiner

*Primary Examiner*—Ralph Gitomer
(74) *Attorney, Agent, or Firm*—Kelly K. Reynolds; Steven J. Hultquist; Intellectual Property/Technology Law

(57) ABSTRACT

The present invention relates to a process for preparing pravastatin sodium. More specifically, in the process for preparing pravastatin sodium by adding a precursor of the pravastatin to a microorganism-culturing medium to obtain pravastatin sodium, the precursor of the pravastatin is added to a culture medium that is culturing *Streptomyces carbophilus* KBT229 (KCCM-10317), which is obtained by UV-mutating a *Streptomyces carbophilus* FERM BP-1145, and cultured to obtain the pravastatin sodium with high density and high efficiency.

2 Claims, No Drawings

PROCESS FOR PREPARING PRAVASTATIN SODIUM

CROSS REFERENCE TO RELATED APPLICATIONS

This application is a national stage filing under 35 U.S.C § 371 of International Application No. PCT/KR02/01824, which claims priority to Korean Patent Application No. 2001/60923, filed Sep. 29, 2001. The entire disclosures of said International Application and Korean Patent Application are hereby incorporated herein by reference in their respective entireties.

FIELD OF THE INVENTION

The present invention relates to a process for preparing pravastatin sodium. More specifically, a the process for preparing pravastatin sodium by adding a precursor of pravastatin to a microorganism-culturing medium, the precursor of pravastatin is added to a culture medium that is culturing *Streptomyces carbophilus* KBT229 (KCCM-10317), which is obtained by UV-mutating a *Streptomyces carbophilus* FERM BP-1145, and cultured to obtain pravastatin sodium with high density and high efficiency.

BACKGROUND OF THE INVENTION

Hyperlipemia is a state in which the amount of lipid increases in the blood. There are four (4) kinds of lipids in the blood—cholesterol, triglyceride (neutral fat), phospholipid and free fatty acid—and cholesterol and triglyceride especially cause clinical problems. Clinically, the following three states in which the amount of cholesterol has increased, the amount of triglyceride has increased, and the amount of both cholesterol and triglyceride has increased are generally called hyperlipemia.

In general, when the concentration of cholesterol is more than 220 mg/dl, triglyceride is more than 150 mg/dl, and HDL-cholesterol is less than 40 mg/dl in the blood serum while fasting, hyperlipemia is diagnosed.

In addition, with regard to the relationship between the cholesterol degree and the incidence rate of hyperlipemia, it is disclosed that when the LDL-cholesterol degree is lowered by 1%, the incidence rate is lowered by about 2%, and when 1 mg/dl of HDL-cholesterol is not taken, the incidence rate is lowered by about 3% (Castelli, JAMA 256:2835, 1986). From the above results, it is known that treating hyperlipemia can result in treating arteriosclerosis.

Generally, as the amount of ingestion of saturated fatty acid decreases and the cholesterol degree in the serum decreases, the incidence rate of ischemic heart disease (coronary artery disease) decreases. However, as the western style of meals and urban life increase the degree of cholesterol, ischemic heart disease also increases.

Therefore, studies and research to invent pharmaceutical agents to reduce the cholesterol degree are widely performed. As a result, pravastatin sodium was found to inhibit the generation of hydroxylmethylglutaryl Co-A (hereinafter, called "HMG Co-A") in the biosynthesis of cholesterol, and was proved to have an effect to treat hyperlipemia.

Conventionally, pravastatin sodium was prepared by adding a precursor of the pravastatin such as compactin to a microorganism-culturing medium and culturing them. Microorganisms that can be used in this method comprise *Streptomyces rhoseochromogenes* NRRL-1233, *Streptomyces rhoseochromogenes* IFO-3363, *Streptomyces rhoseochromogenes* IFO-3411, or the like (U.S. Pat. No. 4,346,227).

Further, a method using *Streptomyces exfoliatus* YJ-118 to prepare the pravastatin sodium is disclosed in KR 210482 B.

However, when pravastatin sodium is prepared by culturing the above microorganisms, the growth of the microorganism is lowered because of the presence of the compactin, and therefore, compactin should be added with low concentration. As a result, the productivity of the pravastatin sodium is low and culturing time becomes long, which reduces efficiency.

At this point, the present inventors studied to prepare the pravastatin sodium with high productivity and efficiency. As seen above, the pravastatin sodium can inhibit generation of cholesterol and be used for treating hyperlipemia, but has the problem that its productivity is low when prepared by using conventional microorganisms, and thus, had a limitation in commercial use. As a result of the study, the present inventors have found that when pravastatin sodium is prepared by culturing a mutant *Streptomyces carbophilus* obtained by mutating *Streptomyces carbophilus*, its productivity becomes high, and have accomplished the present invention.

SUMMARY OF THE INVENTION

Therefore, an object of the present invention is to provide a mutant of *Streptomyces carbophilus* that can prepare the pravastatin sodium with high productivity and density.

An other object of the present invention is to provide a method for preparing pravastatin sodium by using the mutant *Streptomyces carbophilus*.

DETAILED DESCRIPTION OF THE INVENTION

For the above objects, the present invention provides a mutant of *Streptomyces carbophilus*, that is, *Streptomyces carbophilus* KBT229 (KCCM-10317), which prepares the pravastatin sodium with high density.

Further, the present invention provides a method for preparing pravastatin sodium with high productivity and high efficiency, by adding a precursor of the pravastatin to a culture medium that is culturing *Streptomyces carbophilus* KBT229 (KCCM-10317), and culturing them.

Hereinafter, the present invention is described in detail.

The present invention relates to a method for preparing pravastatin sodium, which is prepared by enzyme hydroxyationl reaction and can be used for treating hyperlipemia, with high productivity, by adding a precursor of the pravastatin sodium to a microorganism or microorganism-culturing medium.

In the present invention, a mutant of *Streptomyces carbophilus* was used as a microorganism to prepare pravastatin sodium with high productivity.

That is, after mutating *Streptomyces carbophilus* FERM BP-1145 with UV, a mutant that shows increased productivity of pravastatin sodium was identified, and named "*Streptomyces carbophilus* KBT229" and deposited in Korean Culture Center of Microorganisms on Sep. 20, 2001 under the Budapest Treaty with an international deposit number "KCCM-10317".

The method for preparing pravastatin sodium by using *Streptomyces carbophilus* KBT229 (KCCM-10317) is as follows. First, *Streptomyces carbophilus* KBT229 (KCCM-10317) is inoculated to a first medium (glucose 0.5~2.0%, extract of yeast 0.3~2.0%, polypeptone 0.1~1.0% and potassium phosphate 0.1~0.5%), and shake cultured for 2~3 days, then inoculated to a second medium (glucose 0.5~2.0%, soybean powder 0.5~2.0%, extract of yeast 0.3~1.0%, potassium phosphate 0.1~0.5% and magnesium sulfate 0.01~0.05%) then shake cultured again.

A precursor of the pravastatin sodium is then added to the above cultured microorganism-culturing medium with an amount of 0.02~0.06 wt % to total amount of the culture medium, and shake cultured at 25~29° C., then the pravastatin sodium prepared is separated and purified. In the separation and purification steps, microorganism-cultured medium is centrifuged to remove microorganisms, and the supernatant is absorbed to an absorption column resin, then the column is washed and the pravastatin sodium absorbed is dissolved into an organic solvent, and the dissolved solution is repeatedly proceeded to a liquid chromatography to obtain purified pravastatin sodium.

According to the present invention, the pravastatin sodium may be prepared in a large fermentation chamber with 5 l or 30 l capacity. When pravastatin sodium is prepared in a fermentation chamber, it is preferable to maintain the concentration of the precursor of the pravastatin at the most suitable state according to the fermentation time by adding the precursor of the pravastatin continuously. In addition, it is also preferable to maintain the concentration of glucose at a suitable state by adding glucose continuously.

Hereinafter, the present invention is described in detail with reference to the examples and experimental examples, however, the scope of the present invention is not restricted thereto.

EXAMPLE 1

Producing Mutants of *Streptomyces carbophilus* FERM BP-1145

As a parent strain, *Streptomyces carbophilus* FERM BP-1145 was cultured until reaching the logarithmic growth phase. The cultured medium was centrifuged with 4,000 rpm for 15 minutes, and supernatant liquid was removed to isolate the strain body. 0.85% of a physiological salt solution was added to the strain body and suspended, and then the suspended solution was poured into a sterilized glass Petri dish, and UV was applied thereto for 25 seconds to induce mutation. After applying UV, the Petri dish was wrapped with foil to prevent photoreaction, and stored in the refrigerator for dark reaction for two hours. Samples were collected from the glass Petri dish, and smeared in an agar culture medium (sterile peptone 10 g/l, glucose 20 g/l, agar 20 g/l, extract of yeast 1 g/l) and cultured to obtain ninety (90) colonies.

To identify the strains having tolerance to the compactin, the above-obtained ninety (90) strains of colonies were inoculated to agar culture medium containing compactin (sterile peptone 10 g/l, glucose 20 g/l, agar 20 g/l, extract of yeast 1 g/l, compactin (from Sigma) 1 g/l) by means of platinum loop, and cultured for 5 days, to obtain thirty one (31) strains.

EXAMPLE 2

Selection of *Streptomyces carbophilus* Mutant

Among the above-obtained strains, the strains having excellent enzyme hydroxylation activity were selected as follows.

Each of the strains obtained in Example 1 was inoculated to a 500 ml baffled conical flask containing 100 ml of culture medium (pH 7.0; glucose 0.5~2.0%, extract of yeast 0.3~2.0%, polypeptone 0.1~1.0% and potassium phosphate 0.1~0.5%), and shake cultured at 28° C. and 140 rpm for two days. Each culture of the strains was then inoculated to a 2 l baffled flask containing 400 ml of culture medium (pH 7.0; glucose 0.5~2.0%, soybean powder 0.5~2.0%, extract of yeast 0.3~1.0%, potassium phosphate 0.1~0.5% and magnesium sulfate 0.01~0.05%) with an amount of 40 ml respectively, and shake cultured at 28° C. and 150 rpm for one day, then compactin 160 mg (0.04% (w/v)) and glucose 2.0 g (0.5%) were added to each flask with one day interval. Each flask was then shake cultured at 28° C. and 150 rpm for six days.

After culture, the pH of the culture medium was controlled to pH 9 and stirred for two hours at room temperature, then centrifuged to remove the strain body. The supernatant liquid was passed a column packed with HP-20 resin (manufactured by Samyang Co.) to adsorb the pravastatin sodium, and the column was washed with distilled water controlled to pH 7.0~8.0. After washing, the pravastatin sodium adsorbed was eluted by using 50% (v/v) of aqueous acetone or 50% (v/v) of aqueous ethanol, preferably 50% (v/v) of aqueous ethanol in this example, to obtain a fraction containing pravastatin sodium. The fraction was vacuum condensed, then proceeded to liquid chromatography collector (column: Symmatric C18, 50%(v/v) aqueous ethanol, 1 ml/min) repeatedly and purified. The results are shown in Table 1.

TABLE 1

| Strain | The amount of pravastatin sodium (mg) | PH | PMV*(%) |
|---|---|---|---|
| Mutant 1 | 800 | 7.88 | 12 |
| Mutant 2 | 134 | 7.71 | 10 |
| Mutant 3 | 92 | 7.56 | 6 |
| Mutant 4 | 245 | 7.64 | 9 |
| Mutant 5 | 231 | 7.55 | 10 |
| Mutant 6 | 155 | 7.62 | 10 |
| Mutant 7 | 230 | 7.90 | 11 |
| Mutant 8 | 301 | 7.94 | 11 |
| Mutant 9 | 112 | 7.89 | 12 |
| Mutant 10 | 100 | 7.57 | 8 |
| Mutant 11 | 85 | 7.34 | 6 |
| Mutant 12 | 211 | 7.66 | 10 |
| Mutant 13 | 210 | 7.70 | 10 |
| Mutant 14 | 60 | 7.66 | 9 |
| Mutant 15 | 108 | 7.77 | 10 |
| Mutant 16 | 99 | 7.59 | 9 |
| Mutant 17 | 200 | 7.71 | 11 |
| Mutant 18 | 266 | 7.89 | 12 |
| Mutant 19 | 104 | 7.85 | 10 |
| Mutant 20 | 88 | 7.76 | 10 |
| Mutant 21 | 205 | 7.96 | 11 |
| Mutant 22 | 310 | 7.84 | 10 |
| Mutant 23 | 307 | 7.54 | 11 |
| Mutant 24 | 407 | 7.30 | 13 |
| Mutant 25 | 325 | 7.74 | 12 |
| Mutant 26 | 465 | 7.58 | 11 |
| Mutant 27 | 287 | 7.89 | 10 |
| Mutant 28 | 103 | 7.55 | 9 |
| Mutant 29 | 99 | 7.78 | 9 |
| Mutant 30 | 456 | 7.87 | 13 |
| Mutant 31 | 304 | 7.89 | 12 |

From the above result, the Mutant 1 having the most efficient ability of preparing pravastatin sodium was selected, named *Streptomyces carbophilus* KBT229, and deposited in the Korean Culture Center of Microorganisms on Sep. 20, 2001 with deposit number KCCM-10317.

EXPERIMENTAL EXAMPLE 1

Comparison of the Productivity of Pravastatin Sodium

The amount of the pravastatin sodium produced by using *Streptomyces carbophilus* FERM BP-1145 was measured with the method of Example 2.

As a result, the amount of the pravastatin sodium produced by using *Streptomyces carbophilus* FERM BP-1145 was 200 mg. Therefore, it is concluded that the productivity of the pravastatin sodium by *Streptomyces carbophilus* KBT 229 is four times more than that of the *Streptomyces carbophilus* FERM BP-1145.

EXPERIMENTAL EXAMPLE 2

Measurement of the Productivity of Pravastatin Sodium when the Precursor of Pravastatin was Continuously Added

*Streptomyces carbophilus* KBT229 was cultured with the method of Example 2. That is, *Streptomyces carbophilus* KBT229 was cultured in a 2 l flask containing 250 ml of culture medium for one day, and inoculated to a 5 l capacity of Jar fermentor containing 2.5 l of sterilized culture medium (pH 7.0; glucose 0.5~2.0%, soybean powder 0.5~2.0%, extract of yeast 0.3~1.0%, potassium phosphate 0.1~0.5% and magnesium sulfate 0.01~0.05%), then cultured at 28° C. and 400 rpm for one day. Then, compactin, the precursor of pravastatin and 25% of glucose were continuously added, while controlling the concentration of the precursor to the culture medium, measured by HPLC quantitative analysis, to be 0.04~0.06% for the first 60 hours, then 0.02~0.04% after 60 hours to 120 hours. Then, the precursor was not added after 120 hours to make the concentration 0% after 144 hours (6 days). The amount of 25% glucose in the medium was controlled to be 0.1~0.4%.

The conditions for the quantitative analysis of the precursor by HPLC analysis were as follows. The culture medium underwent extraction by using 100% methanol in which 0.02N NaOH was dissolved, and centrifuged and filtered, then analyzed under the following conditions; solvents containing 77% of methanol, 0.1% of acetic acid, 0.1% of trimethylamine and 22.8% of water; 25° C. temperature; C18 (Symmetry) column; 1 ml/min of flow rate; and 238 nm of wavelength.

After culture, 13.2 g of purified pravastatin sodium was obtained. The same culture was performed in a 30 l fermentation chamber, and the same amount of pravastatin sodium was obtained.

USEFULNESS IN INDUSTRY

As seen above, pravastatin sodium can be prepared with excellent productivity by adding a precursor of pravastatin to a culturing medium of *Streptomyces carbophilus* KBT229 (KCCM-10317) then culturing. By using this method pravastatin sodium can be prepared on a large scale such as in 5 l or 30 l fermentation chambers, and therefore can be applied in industry.

The invention claimed is:

1. *Streptomyces carbophilus* KTB229 (KCCM-10317) having enhanced productivity of pravastatin sodium.

2. A method for preparing pravastatin sodium by adding a precursor of pravastatin to a microorganism or a culturing medium of a microorganism, and culturing the microorganism in said culturing medium wherein the microorganism is *Streptomyces carbophilus* KTB229 (KCCM-10317).

* * * * *